(12) United States Patent
Van Kruchten et al.

(10) Patent No.: US 6,580,008 B2
(45) Date of Patent: Jun. 17, 2003

(54) CATALYTIC PROCESS FOR PRODUCING AN ALKYLENE GLYCOL WITH REACTOR-OUTPUT RECYCLE

(75) Inventors: Eugene Marie Godfried Andre Van Kruchten, Amsterdam (NL); Willem Derks, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/964,169

(22) Filed: Sep. 26, 2001

(65) Prior Publication Data

US 2002/0082456 A1 Jun. 27, 2002

(30) Foreign Application Priority Data

Sep. 28, 2000 (EP) .............................. 00203387

(51) Int. Cl.⁷ ........................ C07C 27/00; C07C 29/00; C07C 27/26; C07C 29/74
(52) U.S. Cl. ....................... 568/867; 568/872
(58) Field of Search ................... 568/867, 872

(56) References Cited

U.S. PATENT DOCUMENTS

| 4,571,440 A | 2/1986 | Keen et al. ............ 568/872 |
| 5,064,804 A | 11/1991 | Soo et al. ................. 502/335 |
| 6,124,508 A | 9/2000 | Van Kruchten ........... 568/867 |

FOREIGN PATENT DOCUMENTS

| EP | 0156449 A2 | 10/1985 | ......... C07C/29/10 |
| EP | 0160330 A1 | 11/1985 | ......... C07C/31/20 |
| EP | 0529726 A1 | 3/1993 | ......... C07C/29/10 |
| RU | 2002726 | 5/1992 | ......... C07C/29/10 |
| WO | WO 95/20559 | 8/1995 | ......... C07C/29/10 |
| WO | WO 99/31033 | 6/1999 | ......... C07C/29/10 |
| WO | WO 99/31034 | 6/1999 | ......... C07C/29/10 |
| WO | WO 00/35840 | 6/2000 | ......... C07C/29/10 |

*Primary Examiner*—Samuel Barts
*Assistant Examiner*—Sikarl A. Witherspoon

(57) ABSTRACT

A process for the production of an alkylene glycol comprising:

a feed mixture containing a respective alkylene oxide and water is introduced to at least one inlet of a reactor containing a fixed bed of a solid catalyst based on an anion exchange resin, and a reactor output mixture containing an alkylene glycol and unreacted feed mixture is removed from at least one outlet of the reactor, a characterised in that at least a part of the reactor output mixture is recycled to at least one inlet of the same reactor.

61 Claims, No Drawings

CATALYTIC PROCESS FOR PRODUCING AN ALKYLENE GLYCOL WITH REACTOR-OUTPUT RECYCLE

The present invention relates to a process for producing an alkylene glycol by reacting an alkylene oxide with water in the presence of a catalytic composition.

BACKGROUND OF THE INVENTION

Alkylene glycols, in particular monoalkylene glycols, are of established commercial interest. For example, monoalkylene glycols are being used in anti-freeze compositions, as solvents and as base materials in the production of polyalkylene terephtalates e.g. for fibres and bottles.

The production of alkylene glycols by liquid phase hydrolysis of alkylene oxide is known. The hydrolysis is performed without a catalyst by adding a large excess of water, e.g. 20 to 25 moles of water per mole of alkylene oxide, or it is performed with a smaller excess of water in a catalytic system. The reaction is considered to be a nucleophilic substitution reaction, whereby opening of the alkylene oxide ring occurs, water acting as the nucleophile. Because the primarily formed monoalkylene glycol may also act as a nucleophile, as a rule a mixture of monoalkylene glycol, dialkylene glycol and higher alkylene glycols is formed. In order to increase the selectivity to monoalkylene glycol, it is necessary to suppress the secondary reaction between the primary product and the alkylene oxide, which competes with the hydrolysis of the alkylene oxide.

One effective means for suppressing the secondary reaction is to increase the relative amount of water present in the reaction mixture. Although this measure improves the selectivity towards the production of the monoalkylene glycol, it creates a problem in that large amounts of water have to be removed for recovering the product.

Considerable efforts have been made to find an alternative for increasing the reaction selectivity without having to use a large excess of water. Usually these efforts have focused on the selection of more active hydrolysis catalysts and various catalysts have been disclosed.

Both acid and alkaline hydrolysis catalysts have been investigated, whereby it would appear that the use of acid catalysts enhances the reaction rate without significantly affecting the selectivity, whereas by using alkaline catalysts generally lower selectivities with respect to the monoalkylene glycol are obtained.

Certain anions, e.g. bicarbonate (hydrogen carbonate), bisulphite (hydrogen sulphite), formate and molybdate, are known to exhibit good catalytic activity in terms of alkylene oxide conversion and selectivity towards monoalkylene glycol. However when the salts of these anions are used as the catalyst in a homogeneous system, work-up of the reaction product by distillation will pose a problem because the salts are poorly soluble in the glycol and tend to make it semisolid.

High conversions, good selectivity and a low water/alkylene oxide ratio can be obtained with the process, disclosed in EP-A 0 156 449 and EP-A 0 160 330 (both of Union Carbide). According to these documents the hydrolysis of alkylene oxides is carried out in the presence of a selectivity-enhancing metalate anion-containing material, preferably a solid having electropositive complexing sites having affinity for the metalate anions. The said solid is preferably an anion exchange resin, in particular a styrene-divinyl benzene copolymer. The electropositive complexing sites are in particular quaternary ammonium, protonated tertiary amine or quaternary phosphonium. The metalate anions are specified as molybdate, tungstate, metavanadate, hydrogen pyrovanadate and pyrovanadate anions. A complication of this process is that the alkylene glycol-containing product stream also comprises a substantial amount of metalate anions, displaced from the electropositive complexing sites of the solid metalate anion containing material. In order to reduce the amount of metalate anions in the alkylene glycol product stream, this stream is contacted with a solid having electropositive complexing sites associated with anions which are replaceable by the said metalate anions.

In U.S. Pat. No. 5,064,804 and in EP-A 0 529 726 (both of Union Carbide) there are disclosed solid catalysts comprising a metalate complexed with a hydrotalcite-type clay. In both specifications it is mentioned that the subject process can be carried out either as a batch or a continuous process with recycle of unconsumed reactants if required. Recycle of reactor output is not mentioned.

In RU-C 2 002 726 (Shvets et al.) there is disclosed a process for the production of alkylene glycols by catalytic hydration of alkylene oxides, whereby alkylene glycol is added to the starting mixture. No recycle of reactor output is mentioned.

In WO 95/20559 (Shell) there is disclosed a process for the preparation of alkylene glycols wherein an alkylene oxide is reacted with water in the presence of a catalyst composition comprising a solid material having one or more electropositive sites, in particular a strongly basic anion exchange resin of the quaternary ammonium type, which electropositive sites are coordinated with one or more anions other than metalate or halogen anions, e.g. bicarbonate, bisulphite and carboxylate—with the proviso that when the solid material is an anionic exchange resin of the quaternary ammonium type and the anion is bicarbonate the process is performed in the substantial absence of carbon dioxide.

A drawback shared by the conventional anionic exchange resins is their limited tolerance to heat and their susceptibility to swelling.

For example, in WO 99/31033 (Dow) it is described how processes comprising anion exchange resins, e.g. as described in WO 95/20559, suffer from undesirable swelling, particularly at temperatures greater than 95° C. This document further describes a method of minimising such swelling comprising adding to the reaction mixture a combination of additives comprising carbon dioxide and a base in an amount sufficient to maintain a pH between 5.0 and 9.0.

Further, WO 99/31034 (Dow) proposes a method of minimising the swelling of an anion exchange resin by using an adiabatic reactor. In one embodiment two or more adiabatic reactors are operated in series, each reactor containing a separate batch of catalyst.

Catalyst swelling is problematic as it can result in flow of reactants through the reactor being slowed or blocked. Therefore, it would be advantageous if there was a means by which swelling of a catalyst based on an anion exchange resin employed in the conversion of alkylene oxides to alkylene glycols could be minimised and/or the life-time of that catalyst prolonged.

SUMMARY OF THE INVENTION

The present invention provides a process for the production of an alkylene glycol comprising:

a) introducing a feed mixture comprising an alkylene oxide and water to at least one inlet of a reactor containing a fixed bed of a solid catalyst based on an anion exchange resin, and b) removing a reactor output mixture comprising an alkylene glycol and unreacted feed mixture from at least one outlet of the reactor, c) recycling at least a part of the reactor output mixture to at least one inlet of the same reactor.

DETAILED DESCRIPTION OF THE INVENTION

It has now been found that by recycling reactor output from a reactor containing a catalyst based on an anion exchange resin back through the same reactor, swelling of the catalyst may be reduced.

In the present invention, a part of the reactor output is recycled to at least one inlet of the same reactor. The part of the reactor output to be recycled may be conveniently separated from the part not to be recycled after the reactor output has left the reactor; or alternatively the part of the reactor output to be recycled may be conveniently removed from the reactor via a different outlet of the reactor than that from which the part of the reactor output not to be recycled is removed.

Accordingly, in one preferred embodiment of the present invention, an outlet of the reactor for the part of the reactor output mixture which is to be recycled is positioned upstream of an outlet of the reactor for the part of the reactor output mixture which is not to be recycled.

In a further preferred embodiment, an outlet of the reactor for the part of the reactor output mixture which is to be recycled is positioned downstream of an outlet of the reactor for the part of the reactor output mixture which is not to be recycled.

In a most preferred embodiment, the part of the reactor output to be recycled is separated from the part not to be recycled after the reactor output has left the reactor.

In the present invention the part of the reactor output to be recycled may be recycled to a reactor inlet leading directly to the reactor, or it may be first mixed with a water and/or alkylene oxide feed stream on route to the reactor. Conveniently, the part of the reactor output mixture to be recycled is first mixed with a feed mixture comprising an alkylene oxide and water, and the combined mixture of recycled reactor output, alkylene oxide and water then introduced to at least one inlet of the reactor.

The amount of reactor output mixture to be recycled may be varied to obtain optimum performance with regard to other reaction parameters employed, however it is preferred that the part of the reactor output which is recycled is in the range of from 50 to 99.5 wt % of the total reactor output, more preferably in the range of from 75 to 99.5 wt %, and most preferably in the range of from 80 to 99.5 wt %.

The temperature of the present process is preferably in the range of from 60° C. to 200° C., more preferably in the range of from 70° C. to 110° C., and most preferably in the range of from 80° C. to 110° C.

In the present invention, it has been shown that recycling a part of a reactor output mixture back through the same reactor reduces catalyst swelling. The exact reasons for this surprising effect are as yet unknown. However, one possible explanation is that a constituent of the reactor output is reducing swelling; i.e. a positive back-mixing effect is occurring wherein the reactor output comprises one or more constituents not present in the reactants which reduce swelling. Alternatively, the reduction in swelling may be due to increased superficial velocity of reactants through the catalyst bed; the decreased temperature gradient between the reactor inlet and the reactor outlet, or a combination of these and/or other factors.

In the process of the present invention the rate of catalyst swelling is preferably kept to less than 1%/100 hrs.

A further advantageous feature of the present invention is that by recycling a part of the reactor output mixture back into the reactor, any temperature difference that may arise between the top and the bottom of the reactor is minimised. Accordingly, less external temperature control is required to maintain the reaction temperature than with a conventional reactor. This is particularly advantageous when isothermal conditions are preferred.

The process of the present invention may be implemented in an isothermal or an adiabatic reactor. However, the present invention has been found to give particularly good results in terms of minimising catalyst swelling when the reactor is an isothermal reactor and in a particularly preferred embodiment of the present invention the reactor is an isothermal reactor.

Isothermal reactors are generally shell and tube reactors, mostly of the multitubular type wherein the tubes contain the catalyst and the temperature is controlled by passing a fluid or gas outside the tubes. Prior to the present invention isothermal reactors were thought to be inappropriate for use with anion exchange resin catalysts as in order to control effectively the temperature during reaction, the reactor tubes of isothermal reactors needed to be long and narrow. Accordingly, catalyst expansion resulted in the flow of reactants through the catalyst bed being prevented.

That the present invention reduces swelling in an isothermal reactor is especially surprising as it had been previously taught (WO 99/31034:Dow) that adiabatic reactors were required to minimise catalyst swelling.

The process of the present invention may be operated using a single reactor, or using two or more reactors in series wherein the part of the reactor output mixture not to be recycled is passed through at least one further reactor. In this instance the at least one further reactor may be a conventional reactor or it may conveniently be a recycle reactor operated according to the process of the present invention.

The catalyst to be used in the present invention is based on an anion exchange resin. Any of a large number of anion exchange resins can be used in the solid catalyst of the present invention. Examples of anion exchange resins on which the catalyst may conveniently be based include basic quaternary ammonium resins, quaternary phosphonium resins, protonated tertiary amine resins, vinylpyridine resins, and polysiloxanes.

Preferably, the catalyst is based on a strongly basic quaternary ammonium resin or a quaternary phosphonium resin. The catalyst is most preferably based on an anion exchange resin comprising a trimethylbenzyl ammonium group.

Examples of commercially available anion exchange resins on which the catalyst of the present may be based include Lewatit M 500 WS (Lewatit is a trade mark), Duolite A 368 (Duolite is a trademark) and Amberjet 4200, (all based on polystyrene resins, cross-linked with divinyl benzene) and Reillex HPQ (based on a polyvinylpyridine resin, cross-linked with divinyl benzene)

The anion exchange resin in the fixed bed of solid catalyst may comprise more than one anion. Preferably, the anion is selected from the group of bicarbonate, bisulfite, metalate and carboxylate anions.

When the anion is a carboxylate anion, it is preferred that the anion is a polycarboxylic acid anion having in its chain molecule one or more carboxyl groups and one or more carboxylate groups, the individual carboxyl and/or carboxylate groups being separated from each other in the chain molecule by a separating group consisting of at least one atom. Preferably the polycarboxylic acid anion is a citric acid derivative, more preferably a mono-anion of citric acid.

Most preferably the anion is a bicarbonate anion.

A solid catalyst which has given particularly good results when employed in the process of the present invention, is a catalyst based on a quaternary ammonium resin, preferably a resin comprising a trimethylbenzyl ammonium group, and wherein the anion is a bicarbonate anion.

The catalyst anion may be coordinated with the anion exchange resin by adding an aqueous solution of a suitable neutral or weakly acidic precursor compound to the anion exchange resin, which may or may not have been adapted in a foregoing preparatory step. For example, when the anion exchange resin is a quaternary ammonium resin and the anion is a bicarbonate, the catalyst may be prepared in a single step by adding to an anion exchange resin in the chloride form an aqueous solution of an alkali metal bicarbonate such as sodium bicarbonate, followed by washing with water, or alternatively the catalyst may be prepared in two steps by first converting the resin to the hydroxyl form with a hydroxide such as aqueous sodium hydroxide, and subsequently adding carbon dioxide gas, followed by washing with water.

A stabilising additive may optionally be added to the catalyst bed. Preferably, the stabilising additive is an acidic ion exchange resin, for example a weakly acidic ion exchange resin of the methacrylate type.

The alkylene oxides used as starting materials in the process of the present invention, have their conventional definition, i.e. they are compounds having a vicinal oxide (epoxy) group in their molecules.

Preferred alkylene oxides are alkylene oxides of the general formula:

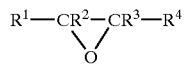

wherein each of $R^1$ to $R^4$ independently represents a hydrogen atom or an optionally substituted alkyl group having from 1 to 6 carbon atoms. Any alkyl group, represented by $R^1$, $R^2$, $R^3$ and/or $R^4$, preferably has from 1 to 3 carbon atoms. Optional substituents on the alkyl groups are inactive moieties such as hydroxy groups. Preferably, $R^1$, $R^2$, and $R^3$ represent hydrogen atoms and $R^4$ represents a non-substituted $C_1$–$C_3$-alkyl group and, more preferably, $R^1$, $R^2$, $R^3$ and $R^4$ all represent hydrogen atoms.

Examples of alkylene oxides which may conveniently be employed include ethylene oxide, propylene oxide, 1,2-epoxybutane, 2,3-epoxybutane and glycidol. The alkylene oxide is preferably ethylene oxide or propylene oxide; ethylene glycol and propylene glycol being alkylene glycols of particular commercial importance. Most preferably the alkylene oxide of the present invention is ethylene oxide and the alkylene glycol is ethylene glycol.

The process of the present invention is preferably performed without using excessive amounts of water. In the process according to the present invention, the amount of water is preferably in the range of from 1 to 35 moles per mole of alkylene oxide, more preferably in the range of from 1 to 25 and most preferably of from 1 to 15.

In the present invention optimal liquid hourly space velocity through the reactor will vary depending on other reaction parameters, however it is preferably in the range of from 1 to 15 l/l.h, more preferably 1 to 10 l.l/ h and most preferably 1 to 5 l/l. h.

In certain embodiments of the present invention it may be beneficial to add carbon dioxide to the reactor. Such carbon dioxide may either be added directly to the reactor or it may be added to the alkylene oxide feed, the water feed, and/or a recycle stream. If carbon dioxide is to be added, the amount of carbon dioxide added may be varied to obtain optimum performance in relation to other reaction parameters, in particular the type of catalyst employed, however the amount added will preferably be less than 0.1% wt, more preferably less than 0.01% wt, based on a total amount of reactants.

The process of the invention may optionally be performed under pressure. When the reaction is performed under pressure, the pressure is conveniently in the range of from 200 to 3000, more conveniently 200 to 2000 KPa.

The present invention further provides a recycle reactor suitable for use in accordance with the process of the present invention.

The present invention will be further understood from the following illustrative examples.

Examples according to the invention were performed in an isothermal recycle reactor, whilst comparative examples were performed in a conventional adiabatic reactor.

Recycle Reactor

The recycle reactor comprised a reactor tube filled with catalyst. The reactor tube had an internal diameter of 9.2 mm and a length of 53 cm. The reactor was isothermal, being fitted with a heating jacket heated by a thermostatically controlled hot oil system. The reactor was fitted with a recycle loop running from a reactor output pipe to a reactor inlet pipe; the recycle loop being heated with temperature controlled electrical tape. A recycle stream was maintained with a gear-pump and the recycle flow measured with a Rosemount Corriolis meter. In operation, a feed mixture containing alkylene oxide and water is fed into the reactor through a reactor inlet wherein it passes through the reactor tube and exits from the reactor as a reactor output mixture; a part of said reactor output mixture being recycled through the recycle loop to the feed mixture of alkylene oxide and water.

Conventional Reactor

Comparative examples were performed in a conventional adiabatic type reactor which comprised a reactor tube filled with catalyst and fitted inside a stainless steel pipe. The reactor tube had an internal diameter of 20 mm and a length of 24 cm. The reactor tube was insulated with a Teflon layer placed between the tube and the stainless steel pipe. The stainless steel pipe was electrically heated to compensate for heat loss only. In operation water was preheated prior to mixing with alkylene oxide to achieve the required inlet temperature.

Preparation of Catalyst

A solid catalyst (A) based on a quaternary ammonium resin and having a bicarbonate anion was prepared by washing an ion exchange resin of the quaternary ammonium type in the chloride form (Amberjet 4200, ex-Rhom & Hass, exchange capacity 1.3 meq/ml) as follows:
  i) 150 ml of wet catalyst was slurried in a water filled glass tube,
  ii) the chloride anion was exchanged by treatment with a sodium-bicarbonate solution (10 times molar excess in 2500 g of water) for approximately 5 hours (Liquid Hourly Space Velocity =4 l/l.h)

iii) the exchanged resin was washed with 1200 ml of water for 2 h (LHSV=4 l/l.h)

In the resulting catalyst the chloride anions from the Amberjet 4200 had been almost completely exchanged with the desired bicarbonate anions, the final chloride content of the catalyst being 32 ppm.

EXAMPLE 1

(According to the Invention)

A water/ethylene oxide feed (mol ratio 25:1) was pumped at 1000 Kpa pressure over an isothermal (70° C.) recycle reactor containing 15 ml of wet catalyst (A). A liquid recycle stream from the reactor output mixture was maintained at a recycle rate of 83.3% wt; the liquid hourly space velocity (LHSV) through the reactor being 13.6 l/l.h. The overall conversion of ethylene oxide to glycols was 30%.

The recycle reactor was operated for 507 hrs after which time the amount of catalyst swelling, as determined by measuring the volume of catalyst before and after use, was 2.5%; giving a rate of swelling of 0.49% /100 hrs.

EXAMPLE 2

(Comparative)

A water/ethylene oxide feed (mol ratio 36.5:1) was pumped at 1000 Kpa pressure over an adiabatic reactor containing 60 ml of wet catalyst (A). The liquid hourly space velocity (LHSV) through the reactor was 3.9 l/l.h and the inlet temperature was from 68–69° C. and the outlet temperature from 79–82° C. The overall conversion of ethylene oxide to glycols was 60–70%.

The reactor was operated for 500 hrs after which the amount of catalyst swelling was 5.6%; giving a rate of swelling of 1.12% /100 hrs.

EXAMPLE 3

(According to the Invention)

A water/ethylene oxide feed (mol ratio 5–25:1) was pumped at 1000 Kpa pressure over an isothermal recycle reactor containing 25 ml of wet catalyst (A). The water ethylene oxide feed contained 20 ppm of added carbon dioxide. Process parameters were varied during the run: the liquid recycle stream from the reactor output mixture being maintained with a recycle rate of from 98.7% to 99.3% wt; the liquid hourly space velocity (LHSV) through the reactor being from 2.0 to 3.2 l/l.h, and the temperature being in the range of from 75 to 105° C. The overall conversion of ethylene oxide to glycols was from 55–91%.

The recycle reactor was operated for 922 hrs after which time the amount of catalyst swelling, as determined by measuring the volume of catalyst before and after use, was 8.4%; giving a rate of swelling of 0.91% /100 hrs.

EXAMPLE 4

(Comparative)

A water/ethylene oxide feed (mol ratio 20–32:1) was pumped at 1000 Kpa pressure over an adiabatic reactor containing 60 ml of wet catalyst (A). Process parameters were varied during the run: the liquid hourly space velocity (LHSV) through the reactor being from 2.4 to 2.6 l/l.h, the inlet temperature being from 67–74° C. and the outlet temperature from 93–98° C. The overall conversion of ethylene oxide to ethylene glycols was from 94–99%.

The reactor was operated for 900 hrs after which time the amount of catalyst swelling was 19.8%; giving a rate of swelling of 2.22% /100 hrs.

By comparison of working Examples 1 and 3 with comparative Examples 2 and 4 respectively, it can be seen that under analogous conditions significantly less catalyst swelling occurs when using a process according to the present invention than with conventional adiabatic processes.

EXAMPLE 5

(According to the Invention)

To demonstrate the utility of the present invention the recycle reactor employed in Examples 1 and 3 was used to convert ethylene oxide (EO) to ethylene glycol under a wide range of reaction conditions (5a–5u). The reactor was run in continuous operation, and the conversion to ethylene oxide of the reaction and the selectivity of the conversion to mono ethylene glycol (MEG) recorded for each set of conditions.

Carbon dioxide was added to the reactor feed (5m–5u) by premixing a calculated amount of carbon dioxide saturated water stream with the water feed to give the required amount of added carbon dioxide. When a reaction parameter was changed, the conversion and selectivity were allowed to stabilize and the values then recorded.

In Experiment 5, the reactor was operated continuously for 1050 hrs after which time the amount of swelling was 10%; giving a rate of swelling of 0.95%/100 hrs.

The results are shown in Table 1.

TABLE 1

| EX | $H_2O$/EO mol/mol | Recycle (% wt) | Temp. (° C.) | LHSV (l/l.h) | $CO_2$ added (ppm) | EO conv. (mol %) | MEG sel. (mol %) |
|---|---|---|---|---|---|---|---|
| 5a | 23.7 | 99.0 | 70 | 3.1 | 0 | 48.3 | 98.8 |
| 5b | 23.7 | 99.0 | 80 | 3.1 | 0 | 61.4 | 98.2 |
| 5c | 23.7 | 99.0 | 90 | 3.1 | 0 | 79.3 | 98.0 |
| 5d | 23.7 | 99.0 | 100 | 3.1 | 0 | 89.6 | 97.6 |
| 5e | 23.7 | 99.0 | 110 | 3.1 | 0 | 94.0 | 97.3 |
| 5f | 9.8 | 99.4 | 70 | 2.0 | 0 | 62.1 | 97.3 |
| 5g | 9.8 | 99.4 | 80 | 2.0 | 0 | 75.7 | 96.4 |
| 5h | 9.8 | 99.4 | 90 | 2.0 | 0 | 86.8 | 95.6 |
| 5i | 9.8 | 99.4 | 100 | 2.0 | 0 | 92.1 | 95.2 |
| 5j | 9.8 | 99.4 | 110 | 2.0 | 0 | 95.8 | 94.4 |
| 5k | 5.0 | 99.4 | 80 | 2.0 | 0 | 76.9 | 93.7 |
| 5l | 5.0 | 99.4 | 100 | 2.0 | 0 | 91.1 | 91.3 |
| 5m | 10.0 | 99.3 | 90 | 2.0 | 20 | 81.0 | 95.6 |
| 5n | 10.0 | 99.2 | 90 | 2.0 | 20 | 80.5 | 95.6 |
| 5o | 10.0 | 99.1 | 90 | 2.0 | 20 | 80.6 | 95.7 |
| 5p | 10.0 | 99.1 | 90 | 2.0 | 40 | 72.3 | 94.7 |
| 5q | 10.0 | 99.2 | 90 | 2.0 | 40 | 71.9 | 94.9 |
| 5r | 10.0 | 99.2 | 90 | 2.0 | 40 | 72.9 | 94.7 |
| 5s | 10.0 | 99.2 | 90 | 2.0 | 60 | 67.6 | 94.4 |
| 5t | 10.0 | 99.2 | 90 | 2.0 | 60 | 66.3 | 94.1 |
| 5u | 10.0 | 99.3 | 90 | 2.0 | 60 | 66.2 | 93.8 |

We claim:

1. A process for the production of an alkylene glycol comprising:
   a) introducing a feed mixture comprising an alkylene oxide and water to at least one inlet of a reactor containing a fixed bed of a solid catalyst based on an anion exchange resin, and
   b) removing a reactor output mixture comprising an alkylene glycol and unreacted feed mixture from at least one outlet of the reactor,
   c) recycling at least a part of the reactor output mixture to at least one inlet of the same reactor.

2. The process of claim 1 wherein the reactor output mixture recycled is in the range of from 50 to 99.5 wt % of the total reactor output.

3. The process of claim 1 wherein the outlet of the reactor for the reactor output mixture which is to be recycled is positioned upstream of the outlet of the reactor for the reactor output mixture which is not to be recycled.

4. The process of claim 3 wherein the reactor output mixture recycled is in the range of from 50 to 99.5 wt % of the total reactor output.

5. The process of claim 1 wherein the outlet of the reactor for the reactor output mixture which is to be recycled is positioned downstream of the outlet of the reactor for the reactor output mixture which is not to be recycled.

6. The process of claim 5 wherein the reactor output mixture recycled is in the range of from 50 to 99.5 wt % of the total reactor output.

7. The process of claim 1 wherein the reactor is an isothermal reactor.

8. The process of claim 2 wherein the reactor is an isothermal reactor.

9. The process of claim 1 wherein the anion exchange resin is a strongly basic quaternary ammonium resin or quaternary phosphonium resin.

10. The process of claim 2 wherein the anion exchange resin is a strongly basic quaternary ammonium resin or quaternary phosphonium resin.

11. The process of claim 3 wherein the anion exchange resin is a strongly basic quaternary ammonium resin or quaternary phosphonium resin.

12. The process of claim 5 wherein the anion exchange resin is a strongly basic quaternary ammonium resin or quaternary phosphonium resin.

13. The process of claim 1 wherein the catalyst anion is selected from the group consisting of bicarbonate, carboxylate, bisulphite and metalate anions.

14. The process of claim 2 wherein the catalyst anion is selected from the group consisting of bicarbonate, carboxylate, bisulphite and metalate anions.

15. The process of claim 13 wherein the anion is a carboxylate anion which carboxylate anion is a polycarboxylic acid anion having in its chain molecule one or more carboxyl groups and one or more carboxylate groups, the individual carboxyl and/or carboxylate groups being separated from each other in the chain molecule by a separating group consisting of at least one atom.

16. The process of claim 14 wherein the anion is a carboxylate anion which carboxylate anion is a polycarboxylic acid anion having in its chain molecule one or more carboxyl groups and one or more carboxylate groups, the individual carboxyl and/or carboxylate groups being separated from each other in the chain molecule by a separating group consisting of at least one atom.

17. The process of claim 1 wherein the anion exchange resin is a quaternary ammonium resin and the catalyst anion is a bicarbonate anion.

18. The process of claim 1 wherein the alkylene oxide is ethylene oxide and the alkylene glycol is ethylene glycol.

19. The process of claim 2 wherein the alkylene oxide is ethylene oxide and the alkylene glycol is ethylene glycol.

20. The process of claim 9 wherein the alkylene oxide is ethylene oxide and the alkylene glycol is ethylene glycol.

21. The process of claim 13 wherein the alkylene oxide is ethylene oxide and the alkylene glycol is ethylene glycol.

22. The process of claim 17 wherein the alkylene oxide is ethylene oxide and the alkylene glycol is ethylene glycol.

23. The process of claim 1 wherein the part of the reactor output mixture to be recycled is removed from the reactor via a different outlet of the reactor than that from which the part of the reactor output mixture not to be recycled is removed.

24. The process of claim 1 wherein the part of the reactor output mixture to be recycled is separated from the part of the reactor output mixture not to be recycled after the reactor output mixture has left the reactor.

25. The process of claim 1 wherein at least a part of the reactor output mixture is recycled to a reactor inlet leading directly to the reactor.

26. The process of claim 1 wherein the reactor output mixture to be recycled is first mixed with water before entering the reactor.

27. The process of claim 1 wherein the reactor output mixture to be recycled is first mixed into the feed stream before entering the reactor.

28. The process of claim 1 wherein the reactor output mixture to be recycled is first mixed with the alkylene oxide before entering the reactor.

29. The process of claim 2 wherein the reactor output mixture recycled is in the range of from 75 to 99.5 wt % of the total reactor output.

30. The process of claim 1 wherein the reactor is at a temperature in the range of from 60° C. to 200° C.

31. The process of claim 1 wherein the rate of swelling of the solid catalyst is less than 1%/100 hours.

32. The process of claim 7 wherein the reactor is a shell and tube reactor.

33. The process of claim 1 wherein the anion exchange resin is selected from the group consisting of protonated tertiary amine resins, vinylpyridine resins and polysiloxanes.

34. The process of claim 15 wherein the polycarboxylic acid anion is a citric acid derivative.

35. The process of claim 1 wherein a stabilizing additive is added to the catalyst.

36. The process of claim 35 wherein the stabilizing additive is an acidic ion exchange resin.

37. The process of claim 1 wherein the alkylene oxide is of the general formula:

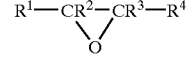

wherein each of the $R^1$ to $R^4$ independently is selected from the group consisting of hydrogen and optionally substituted alkyl groups having 1 to 6 carbon atoms.

38. The process of claim 1 wherein the alkylene oxide is propylene oxide.

39. The process of claim 1 wherein the alkylene oxide is selected from the group consisting of 1,2-epoxybutane, 2,3-epoxybutane and glycidol.

40. The process of claim 1 wherein the amount of water introduced to the reactor is in the range of from 1 to 35 moles per mole of alkylene oxide.

41. The process of claim 40 wherein the amount of water introduced to the reactor is in the range of from 1 to 25 moles per mole of alkylene oxide.

42. The process of claim 1 wherein the liquid hourly space velocity through the reactor is in the range of from 1 to 15 l/l.h.

43. The process of claim 1 wherein carbon dioxide is added to the reactor.

44. The process of claim 1 wherein the reaction is performed under a pressure in the range of from 200 to 3000 KPa.

45. A process for the production of an alkylene glycol comprising:

a) reacting an alkylene oxide and water in the presence of a fixed bed of a solid catalyst based on an anion exchange resin in a reactor comprising at least one inlet and at least one outlet, thereby producing a reaction product mixture comprising the alkylene glycol, b) removing the reactor product mixture through the at least one reactor outlet, thereby providing a reactor output mixture, and c) recycling at least a part of the reactor output mixture to at least one inlet of the same reactor.

46. The process of claim 45 wherein the reactor output mixture recycled is in the range of from 50 to 99.5 wt % of the total reactor output.

47. The process of claim 45 wherein the outlet of the reactor for the reactor output mixture which is to be recycled is positioned upstream of the outlet of the reactor for the reactor output mixture which is not to be recycled.

48. The process of claim 45 wherein the outlet of the reactor for the reactor output mixture which is to be recycled is positioned downstream of the outlet of the reactor for the reactor output mixture which is not to be recycled.

49. The process of claim 45 wherein the reactor is an isothermal reactor.

50. The process of claim 45 wherein the anion exchange resin is selected from the group consisting of strongly basic quaternary ammonium resins and quaternary phosphonium resins.

51. The process of claim 45 wherein the catalyst anion is selected from the group consisting of bicarbonates, carboxylates, bisulphites and metalate anions.

52. The process of claim 51 wherein the anion is a carboxylate anion, said carboxylate anion is a polycarboxylic acid anion having in its chain molecule one or more carboxyl groups and one or more carboxylate groups, the individual carboxyl and/or carboxylate groups being separated from each other in the chain molecule by a separating group comprising at least one atom.

53. The process of claim 45 wherein the anion exchange resin is a quaternary ammonium resin and the catalyst anion is a bicarbonate anion.

54. The process of claim 45 wherein the alkylene oxide is of the general formula:

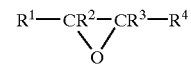

wherein each of the $R^1$ to $R^4$ independently is selected from the group consisting of hydrogen atom and optionally substituted alkyl groups having 1 to 6 carbon atoms.

55. The process of claim 45 wherein the alkylene oxide is ethylene oxide.

56. The process of claim 46 wherein the alkylene oxide is ethylene oxide.

57. The process of claim 50 wherein the alkylene oxide is ethylene oxide.

58. The process of claim 51 wherein the alkylene oxide is ethylene oxide.

59. The process of claim 45 wherein the alkylene oxide is propylene oxide.

60. The process of claim 45 wherein the alkylene oxide is selected from the group consisting of 1,2-epoxybutane, 2,3-epoxybutane and glycidol.

61. The process of claim 45 wherein the amount of water in step a) is in the range of from 1 to 35 moles per mole of alkylene oxide.

* * * * *